US012588853B2

(12) United States Patent
Sharma et al.

(10) Patent No.: US 12,588,853 B2
(45) Date of Patent: Mar. 31, 2026

(54) IDENTIFYING CARDIAC ABNORMALITIES IN MULTI-LEAD ECGS USING HYBRID NEURAL NETWORK WITH FULCRUM BASED DATA RE-BALANCING

(71) Applicant: Tata Consultancy Services Limited, Mumbai (IN)

(72) Inventors: Varsha Sharma, Kolkata (IN); Ayan Mukherjee, Kolkata (IN); Murali Poduval, Mumbai (IN); Sundeep Khandelwal, Noida (IN); Anirban Dutta Choudhury, Kolkata (IN); Chirayata Bhattacharyya, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 398 days.

(21) Appl. No.: 18/329,855

(22) Filed: Jun. 6, 2023

(65) Prior Publication Data

US 2023/0404461 A1     Dec. 21, 2023

(30) Foreign Application Priority Data

Jun. 17, 2022     (IN) ............................. 202221034879

(51) Int. Cl.
| | |
|---|---|
| *A61B 5/346* | (2021.01) |
| *A61B 5/00* | (2006.01) |
| *G06T 1/00* | (2006.01) |

(52) U.S. Cl.
CPC ............ *A61B 5/346* (2021.01); *A61B 5/7267* (2013.01); *G06T 1/00* (2013.01); *G06T 2207/20081* (2013.01); *G06T 2207/20084* (2013.01)

(58) Field of Classification Search
CPC ....... A61B 5/346; A61B 5/7203; A61B 5/725; A61B 5/7264; A61B 5/7267; G06N 3/045;
(Continued)

(56) References Cited

U.S. PATENT DOCUMENTS

| | | | |
|---|---|---|---|
| 10,339,445 B2 | 7/2019 | Yang et al. | |
| 2018/0064388 A1* | 3/2018 | Heneghan | ............. A61B 5/1114 |
| 2022/0203095 A1* | 6/2022 | Libbus | ............... A61N 1/36175 |

OTHER PUBLICATIONS

Akhilesh Kumar Gangwar et al., "Diabetic Retinopathy Detection Using Transfer Learning and Deep Learning," Sep. 2020, 679-689, Springer, https://link.springer.com/chapter/10.1007/978-981-15-5788-0_64.
(Continued)

*Primary Examiner* — George Manuel
(74) *Attorney, Agent, or Firm* — Finnegan, Henderson, Farabow, Garrett & Dunner, LLP

(57) ABSTRACT

State of art techniques hardly provide data balancing for multi-label multi-class data. Embodiments of the present disclosure provide a method and system for identifying cardiac abnormality in multi-lead ECGs using a Hybrid Neural Network (HNN) with fulcrum based data re-balancing for data comprising multiclass-multilabel cardiac abnormalities. The fulcrum based dataset re-balancing disclosed enables maintaining natural balance of the data, control the re-sample volume, and still support the lowly represented classes there by aiding proper training of the DL architecture. The HNN disclosed by the method utilizes a hybrid approach of pure CNN, a tuned-down version of ResNet, and a set of handcrafted features from a raw ECG signal that are concatenated prior to predicting the multiclass output for the ECG signal. The number of features is flexible and enables adding additional domain-specific features as needed.

12 Claims, 9 Drawing Sheets

(58) Field of Classification Search
CPC ...... G06N 3/0464; G06N 3/048; G06N 3/082;
G06N 3/09; G06T 1/00; G06T
2207/20081; G06T 2207/20084
See application file for complete search history.

(56) References Cited

OTHER PUBLICATIONS

Akhilesh Kumar Gangwar et al., "An hybrid ECG-based deep network for the early identification of high-risk to major cardio-vascular events for hypertension patients," Journal of Biomedical Informatics, Jan. 2021, vol. 113, pp. 679-689, Science Direct https://www.sciencedirect.com/science/article/pii/S1532046420302768.

* cited by examiner

300

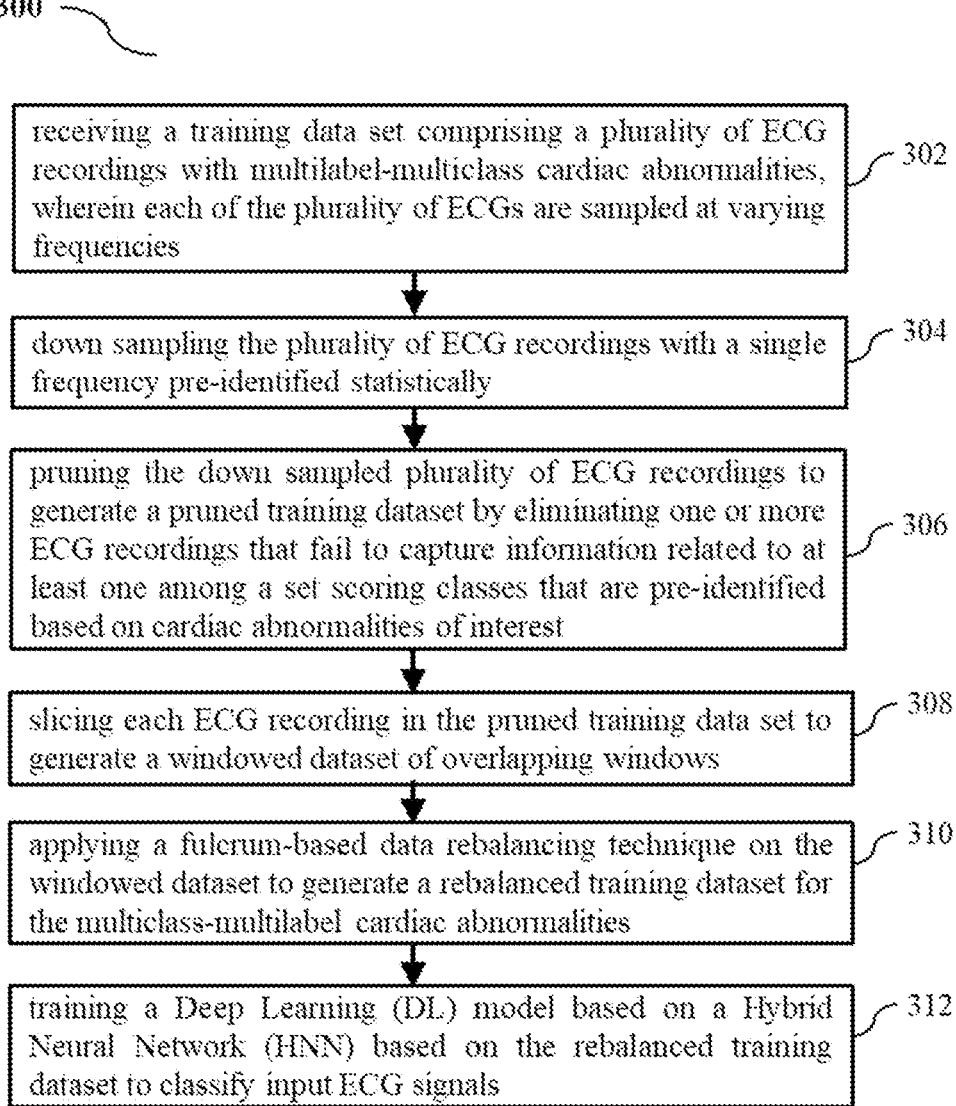

receiving a training data set comprising a plurality of ECG recordings with multilabel-multiclass cardiac abnormalities, wherein each of the plurality of ECGs are sampled at varying frequencies — 302 down sampling the plurality of ECG recordings with a single frequency pre-identified statistically — 304 pruning the down sampled plurality of ECG recordings to generate a pruned training dataset by eliminating one or more ECG recordings that fail to capture information related to at least one among a set scoring classes that are pre-identified based on cardiac abnormalities of interest — 306 slicing each ECG recording in the pruned training data set to generate a windowed dataset of overlapping windows — 308 applying a fulcrum-based data rebalancing technique on the windowed dataset to generate a rebalanced training dataset for the multiclass-multilabel cardiac abnormalities — 310 training a Deep Learning (DL) model based on a Hybrid Neural Network (HNN) based on the rebalanced training dataset to classify input ECG signals — 312

FIG. 3

Class-wise ECG recording distribution

Epoch

IDENTIFYING CARDIAC ABNORMALITIES IN MULTI-LEAD ECGS USING HYBRID NEURAL NETWORK WITH FULCRUM BASED DATA RE-BALANCING

This U.S. patent application claims priority under 35 U.S.C. § 119 to: Indian Patent Application No. 202221034879, filed on 17 Jun. 2022. The entire contents of the aforementioned application are incorporated herein by reference.

TECHNICAL FIELD

The embodiments herein generally relates to the field of clinical predictions using Deep Learning (DL) and, more particularly, to a method and system for identifying cardiac abnormalities in multi-lead electrocardiograms (ECGs) using Hybrid Neural Network (HNN) with fulcrum based data re-balancing for data comprising multiclass-multilabel cardiac abnormalities.

BACKGROUND

Automatic classification of electrocardiograms (ECG) is very important for clinical diagnosis and predictions of cardiovascular diseases in patients. State of the art automated ECG analysis for classification of patient focus on single-label problems, wherein one ECG record corresponds to one label i.e., a single disease such as Atrial Fibrillation (AF), coronary heart disease (CHD). However, in reality an ECG record may contain multiple diseases at the same time, and it is critical to study the multilabel ECG classification. However, conventional Neural Network (NN) based automated cardiac abnormality predictions have been based on single lead ECG. Recently Deep learning (DL) is being explored for classification of cardiac abnormalities using multi-lead ECG dataset. However, there is presence of high imbalance in available multi-lead ECG dataset. Thus, imbalanced dataset affects accuracy of NN models for disease predictions.

Existing algorithms balance the datasets in terms of the most-represented class. High disparity exists among natural datasets (especially clinical data). This results in ballooning of the rebalanced dataset, also the natural balance of the dataset is completely overhauled, following such practices. There hardly exists a technique that provides data balancing for multi-label multi-class data by overcoming above mentioned disparity challenges.

Further, designing an appropriate deep learning NN architecture for multi-label multi-class problems specific to ECG classification is critical for accuracy of classification.

SUMMARY

Embodiments of the present disclosure present technological improvements as solutions to one or more of the above-mentioned technical problems recognized by the inventors in conventional systems.

For example, in one embodiment, a method for identifying cardiac abnormality in multi-lead electrocardiograms (ECGs) using Hybrid Neural Network (HNN) with fulcrum based data re-balancing is provided. The method includes receiving a training data set comprising a plurality of ECG recordings with multilabel-multiclass cardiac abnormalities, wherein each of the plurality of ECGs are sampled at varying frequencies. Further, the method includes down sampling the plurality of ECG recordings with a single frequency pre-identified statistically. Further, the method includes pruning the down sampled plurality of ECG recordings to generate a pruned training dataset by eliminating one or more ECG recordings that fail to capture information related to at least one among a set scoring classes that are pre-identified based on cardiac abnormalities of interest. Further, the method includes slicing each ECG recording in the pruned training data set to generate a windowed dataset of overlapping windows. Furthermore, the method includes applying a fulcrum-based data rebalancing technique on the windowed dataset to generate a rebalanced training dataset for the multiclass-multilabel cardiac abnormalities, the fulcrum-based data rebalancing technique comprising: (a) deriving a fulcrum point ($N_{fulcrum}$) of the windowed dataset from class frequency of each window in the windowed dataset based on one or more class labels from among the set of scoring classes assigned to each window, wherein one or more classes from among the set of scoring classes with class frequency above the fulcrum point are identified as majority classes, wherein classes with class frequency below the fulcrum point are identified as minority classes; and (b) performing a random sampling on the windowed dataset that is identified under minority classes to reach the fulcrum point, wherein random sampling provides a representation at least equal to the fulcrum point to the minority classes, wherein the majority classes are excluded from the random sampling. Furthermore, the method includes training a Hybrid Neural Network (HNN) architecture based DL model using the rebalanced training dataset to classify input ECG signals. Further, the method includes utilizing the trained DL model to classify an input ECG signal of a subject by predicting the abnormalities in the input ECG into one or more classes among the set of scoring classes.

In another aspect, a system for identifying cardiac abnormality in multi-lead electrocardiograms (ECGs) using Hybrid Neural Network (HNN) with fulcrum based data re-balancing is provided. The system comprises a memory storing instructions; one or more Input/Output (I/O) interfaces; and one or more hardware processors coupled to the memory via the one or more I/O interfaces, wherein the one or more hardware processors are configured by the instruction to receive a training data set comprising a plurality of ECG recordings with multilabel-multiclass cardiac abnormalities, wherein each of the plurality of ECGs are sampled at varying frequencies. Further, the one or more hardware processors are configured to down sampling the plurality of ECG recordings with a single frequency pre-identified statistically. Further, the one or more hardware processors are configured to prune the down sampled plurality of ECG recordings to generate a pruned training dataset by eliminating one or more ECG recordings that fail to capture information related to at least one among a set scoring classes that are pre-identified based on cardiac abnormalities of interest. Further, the one or more hardware processors are configured to slice each ECG recording in the pruned training data set to generate a windowed dataset of overlapping windows. Furthermore, the one or more hardware processors are configured to apply a fulcrum-based data rebalancing technique on the windowed dataset to generate a rebalanced training dataset for the multiclass-multilabel cardiac abnormalities, the fulcrum-based data rebalancing technique comprising: (a) deriving a fulcrum point ($N_{fulcrum}$) of the windowed dataset from class frequency of each window in the windowed dataset based on one or more class labels from among the set of scoring classes assigned to each window, wherein one or more classes from among the set of scoring classes with class frequency above the fulcrum point are identified as majority classes, wherein classes with class frequency below the fulcrum point are identified as minority classes; and (b) performing a random sampling on the windowed dataset that is identified under minority classes to reach the fulcrum point, wherein random sampling provides a representation at least equal to the fulcrum point to the minority classes, wherein the majority classes are excluded from the random sampling. Furthermore, the one or more hardware processors are configured to train a Hybrid Neural Network (HNN) architecture based DL model using the rebalanced training dataset to classify input ECG signals. Further, the one or more hardware processors are configured to utilize the trained DL model to classify an input ECG signal of a subject by predicting the abnormalities in the input ECG into one or more classes among the set of scoring classes.

In yet another aspect, there are provided one or more non-transitory machine-readable information storage mediums comprising one or more instructions, which when executed by one or more hardware processors causes a method for identifying cardiac abnormality in multi-lead electrocardiograms (ECGs) using Hybrid Neural Network (HNN) with fulcrum based data re-balancing. The method includes receiving a training data set comprising a plurality of ECG recordings with multilabel-multiclass cardiac abnormalities, wherein each of the plurality of ECGs are sampled at varying frequencies. Further, the method includes down sampling the plurality of ECG recordings with a single frequency pre-identified statistically. Further, the method includes pruning the down sampled plurality of ECG recordings to generate a pruned training dataset by eliminating one or more ECG recordings that fail to capture information related to at least one among a set scoring classes that are pre-identified based on cardiac abnormalities of interest. Further, the method includes slicing each ECG recording in the pruned training data set to generate a windowed dataset of overlapping windows. Furthermore, the method includes applying a fulcrum-based data rebalancing technique on the windowed dataset to generate a rebalanced training dataset for the multiclass-multilabel cardiac abnormalities, the fulcrum-based data rebalancing technique comprising: (a) deriving a fulcrum point ($N_{fulcrum}$) of the windowed dataset from class frequency of each window in the windowed dataset based on one or more class labels from among the set of scoring classes assigned to each window, wherein one or more classes from among the set of scoring classes with class frequency above the fulcrum point are identified as majority classes, wherein classes with class frequency below the fulcrum point are identified as minority classes; and (b) performing a random sampling on the windowed dataset that is identified under minority classes to reach the fulcrum point, wherein random sampling provides a representation at least equal to the fulcrum point to the minority classes, wherein the majority classes are excluded from the random sampling. Furthermore, the method includes training a Hybrid Neural Network (HNN) architecture based DL model using the rebalanced training dataset to classify input ECG signals. Further, the method includes utilizing the trained DL model to classify an input ECG signal of a subject by predicting the abnormalities in the input ECG into one or more classes among the set of scoring classes.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 3 is a flow diagram illustrating a method for identifying cardiac abnormalities in multi-lead electrocardiograms (ECGs) using the HNN with fulcrum based data re-balancing for data comprising multiclass-multilabel cardiac abnormalities, in accordance with some embodiments of the present disclosure.

Figure 1A:
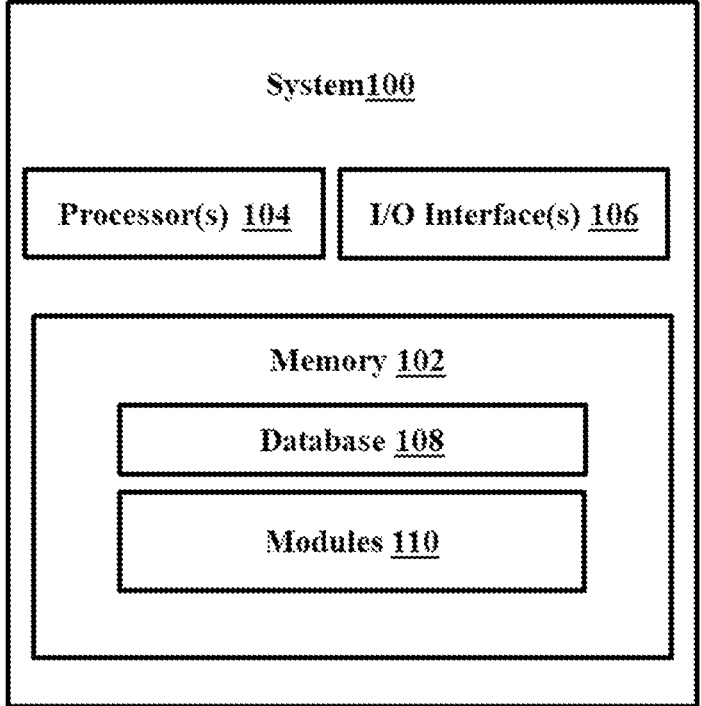
FIG. 1A is a functional block diagram of a system, for identifying cardiac abnormalities in multi-lead electrocardiograms (ECGs) using a Hybrid Neural Network (HNN) with fulcrum based data re-balancing for data comprising multiclass-multilabel cardiac abnormalities, in accordance with some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Multiclass-multilabel cardiac abnormality classification using deep learning (DL) is being currently explored. However, the technical problem of data rebalancing of multiclass-multilabel dataset is hardly addressed by existing data balancing algorithms. Existing data balancing algorithms are designed for binary/multi-class datasets. These existing algorithms balance the datasets in terms of the most-represented class. High disparity exists among natural datasets (especially clinical data). This results in ballooning of the rebalanced dataset, also the natural balance of the dataset is completely overhauled, following such practices. Furthermore, preprocessing techniques and DL based Neural Network (NN) architectures need to be appropriately designed to enhance quality in information extraction and accurate prediction for datasets comprising clinical domain signals, specifically when multi-lead ECG signals are in consideration.

Embodiments of the present disclosure provide a method and system for identifying cardiac abnormalities in multi-lead electrocardiograms (ECGs) using a Hybrid Neural Network (HNN) with fulcrum based data re-balancing for data comprising multiclass-multilabel cardiac abnormalities. The fulcrum based dataset re-balancing disclosed enables modifying the existing balance in data which is skewed in nature to maintain natural balance of the data and controls the re-sample volume, while still supporting the lowly represented classes there by aiding proper training of the DL architecture. A work in the literature '*Multidimensional Balance-based Cluster Boundary Detection for High Dimensional Data*' by Xiaofeng Cao et. al refers to a fulcrum based approach, but the problem considered is that of an effective cluster boundary detection in 12 lead ECG recording data to primarily identify noisy signals. Whereas, in the fulcrum based technique provided by the method disclosed solves a different technical problem of data re-balancing, by removing high variance that exists between the distribution of different classes in a dataset. The above prior art operates on each point of a recording i.e., instance of training data, whereas in the method disclosed the fulcrum operations are based on recording labels (annotations of the training data) alone. Furthermore, requires data normalization as an additional preprocessing step.

Referring to NNs architectures in the art that have been proposed for ECG signal classification for cardiac abnormalities, there are many hybrid NNs that have Convolutional Neural Network (CNN) layers combined with other NN layers such as recurrent neural network (RNN), Long short-term memory (LSTM) and the like. In a prior art such as '*Multiscale Residual Network Based on Channel Spatial Attention Mechanism for Multilabel ECG Classification* by Shuhong Wang et. al use GoogleNet and Residual Network (ResNet), where both their base networks are CNNs but are connected in a different manner which changes their properties and makes them independent from each other and do not provide a true hybrid network The HNN disclosed by the method is a hybrid approach of pure CNN, a tuned-down version of ResNet, and a set of handcrafted features from a raw ECG signal that are concatenated prior to predicting the multiclass output for the ECG signal. The number of features is flexible and enables adding additional domain-specific features as needed.

Referring now to the drawings, and more particularly to FIGS. 1A through 5C, where similar reference characters denote corresponding features consistently throughout the figures, there are shown preferred embodiments and these embodiments are described in the context of the following exemplary system and/or method.

FIG. 1A is a functional block diagram of a system 100, for identifying cardiac abnormalities in multi-lead electrocardiograms (ECGs) using a Hybrid Neural Network (HNN) with fulcrum based data re-balancing for data comprising multiclass-multilabel cardiac abnormalities, in accordance with some embodiments of the present disclosure.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In an embodiment, the system 100 can be implemented in a variety of computing systems including laptop computers, notebooks, hand-held devices such as mobile phones, workstations, mainframe computers, servers, and the like.

The I/O interface(s) 106 can include a variety of software and hardware interfaces, for example, a web interface, a graphical user interface to display the generated target images and the like and can facilitate multiple communications within a wide variety of networks N/W and protocol types, including wired networks, for example, LAN, cable, etc., and wireless networks, such as WLAN, cellular and the like. In an embodiment, the I/O interface (s) 106 can include one or more ports for connecting to a number of external devices or to another server or devices.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

In an embodiment, the memory 102 includes a plurality of modules 110. The plurality of modules 110 include programs or coded instructions that supplement applications or functions performed by the system 100 for executing different steps involved in the process of identifying cardiac abnormality in multi-lead electrocardiograms (ECGs), being performed by the system 100. The plurality of modules 110, amongst other things, can include routines, programs, objects, components, and data structures, which performs particular tasks or implement particular abstract data types. The plurality of modules 110 may also be used as, signal processor(s), node machine(s), logic circuitries, and/or any other device or component that manipulates signals based on operational instructions. Further, the plurality of modules 110 can be used by hardware, by computer-readable instructions executed by the one or more hardware processors 104, or by a combination thereof. The plurality of modules 110 can include various sub-modules such preprocessing block, a Deep Learning model (DL) based on the HNN architecture) and a post processing block as depicted FIG. 1B. The FIG. 1B. is an overview of the system architecture depicting ECG classification pipeline for identifying cardiac abnormalities, in accordance with some embodiments of the present disclosure. It can be understood that data (the ECG recordings) must be sliced to fit into an appropriate DL network in pre-processing, and it must be clubbed together in post-processing to reach the conclusion. Depending on these conditions, the ECG classification pipeline divided into three parts: pre-processing, DL network, and post-processing. Each section is described in conjunction with flow diagram of FIG. 3 and an architectural overview of the HNN used by the system of FIG. 1 as depicted in FIGS. 2A through 2C (collectively referred as FIG. 2).

Further, the memory 102 may comprise information pertaining to input(s)/output(s) of each step performed by the processor(s) 104 of the system 100 and methods of the present disclosure. Further, the memory 102 includes a database 108. The database (or repository) 108 may include a plurality of abstracted piece of code for refinement and data that is processed, received, or generated as a result of the execution of the plurality of modules in the module(s) 110. The database 108 stores a training data set comprising a plurality of ECG recordings and a rebalanced training dataset generated by applying preprocessing and fulcrum based data rebalancing on the training dataset. Although the data base 108 is shown internal to the system 100, it will be noted that, in alternate embodiments, the database 108 can also be implemented external to the system 100, and communicatively coupled to the system 100. The data contained within such external database may be periodically updated. For example, new data may be added into the database (not shown in FIG. 1A) and/or existing data may be modified and/or non-useful data may be deleted from the database. In one example, the data may be stored in an external system, such as a Lightweight Directory Access Protocol (LDAP) directory and a Relational Database Management System (RDBMS). Functions of the components of the system 100 are now explained with reference to steps in flow diagrams in FIG. 1B through FIG. 5C.

FIG. 3 is a flow diagram illustrating a method 300 for identifying cardiac abnormalities in multi-lead electrocardiograms (ECGs) using the HNN with fulcrum based data re-balancing for data comprising multiclass-multilabel cardiac abnormalities, in accordance with some embodiments of the present disclosure.

In an embodiment, the system 100 comprises one or more data storage devices or the memory 102 operatively coupled to the processor(s) 104 and is configured to store instructions for execution of steps of the method 300 by the processor(s) or one or more hardware processors 104. The steps of the method 300 of the present disclosure will now be explained with reference to the components or blocks of the system 100 as depicted in FIGS. 1 and 2 and the steps of flow diagram as depicted in FIG. 3. Although process steps, method steps, techniques or the like may be described in a sequential order, such processes, methods, and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Figure 4A:
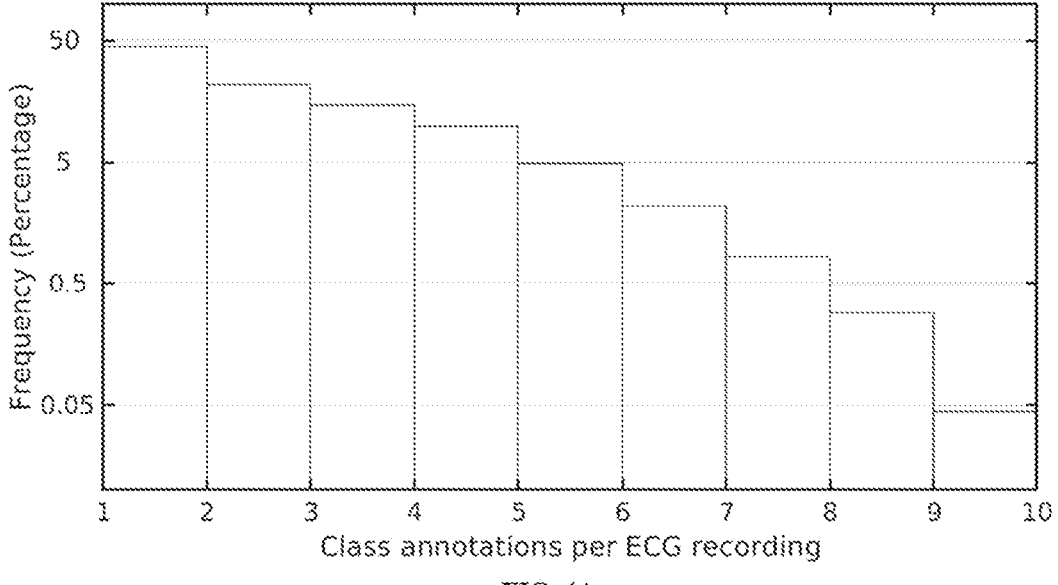
FIGS. 4A, 4B, AND 4C are graphical illustrations depicting characteristics of dataset of ECG recordings used as training dataset for Deep Learning (DL) models to be trained for predicting the multiclass-multilabel cardiac abnormalities, in accordance with some embodiments of the present disclosure.
Figure 4B:
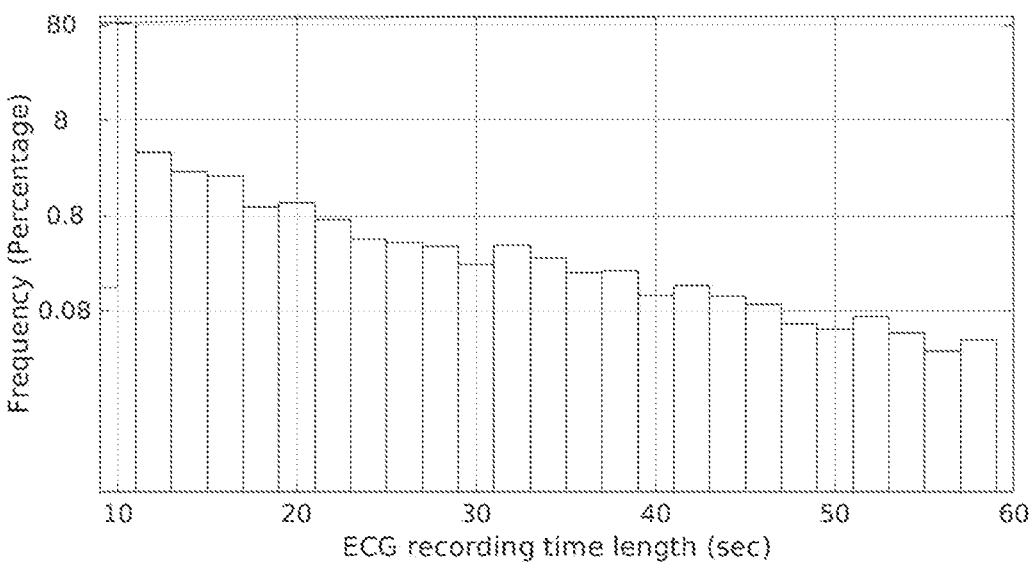

Referring to the steps of the method 300, at step 302 of the method 300, the one or more hardware processors 104 receive the training data set comprising the plurality of ECG recordings with multilabel-multiclass cardiac abnormalities. Each of the plurality of ECGs are sampled at varying frequencies. For example, a total of 43,101 ECG recordings from heterogeneous sources are obtained. Heterogeneity represents diversity in terms of locations on the globe. Different location leads to different environmental conditions while capturing data. Each recording may have more than one abnormality out of the list of 107 abnormalities. These abnormalities are present in terms of their Systematized Nomenclature of Medicine-Clinical Terms (SNOMED-CT) codes along with the gender and age of the patient. FIG. 4A shows that 43% of recordings consist of single abnormality and remaining 57% consist of multiple abnormalities where the count can go up to 8. FIG. 4B shows that 90% of recordings have signal duration around 10 s.

Analysis of data: The analysis of the training data reveals a multitude of challenges. The challenges are discussed in an enumerated manner as follows:

1. Unequal Sampling: The training data comprises of data collected from 6 different geographies. The sampling rate of the subsets differ as well.
2. Class Distribution: The harshest fact regarding the dataset is the unequal distribution of class across the dataset.
3. Similar SNOMED-CT codes: While all class labels have been tagged with unique SNOMED-CT codes, additionally some SNOMED-CT codes have been identified to be similar/equivalent.

5000 unique combinations: The greatest challenge regarding the classification task is the multi-label, multi-class nature of the problem. Within the dataset of 43101 recordings, 5K unique multi class labels are found. The skewed nature of the data distribution can be surmised from the fact that while the highest frequency class the normal class has a representational share of 30%. On the other hand, 500 unique labels has only single representation in the training data making it an extremely difficult classification task and leads to the investigation of its effect on data distribution.

Since ECG recordings (ECG data) is obtained from multiple sources, for example herein from 6 different sources, they need to be down-sampled at single frequency, which is obtained based on statistical analysis. At step 304 of the method 300, the one or more hardware processors 104 down sample the plurality of ECG recordings with a single frequency pre-identified statistically. Typical value of the single sampling frequency is 100 Hz. Mean spectral energies of the ECG recordings across all scoring classes was recorded. It was found that there is a concentration of 95% of the total spectral energy of signals within 0-50 Hz of the spectral map. Hence the signals are down-sampled to 100 Hz following the Nyquist Criteria.

The single frequency for sampling of data obtained from six different ECG sources ranges from 275 Hz to 1 kHz. Spectral analysis is used to bring them the same scale. Following are the steps to select the optimal frequency for down sampling:

Step1: Re-sample all the ECG data to maximum available frequency. The maximum frequency available in data is 1 kHz.

Step2: Calculate the spectral energy for all the 12 channels separately. Spectral Energy=absolute of mean FFT of the signal.

Step3: Calculate percentage of cumulative sum of spectral energy (CSE) for all 12 channels Step4: Filter the frequencies (for each channel) at which CSE reaches for 90%, 95%, 98%, and 99% for the first time.

Step5: Select the optimal down sampling frequency.

From the above steps, a conclusion is reached that 95 percent of the total spectral energy of signals is concentrated within 0-50 Hz of the spectral map. As a result, all signals can be down sampled to 100 Hz using the Nyquist Criteria to capture maximum information in the ECG signal.

Further, it can be noted that evaluation of classifiers has been defined by 'Classification of 12-lead ECGs: the PhysioNet/Computing in Cardiology Challenge 2020', available at https://moody-challenge.physionet.org/2020/. A new scoring metric is developed that awards partial credit to misdiagnoses that result in similar outcomes or treatments as the true diagnoses as judged by cardiologists. This scoring metric reflects the clinical reality that some misdiagnoses are more harmful than others and should be scored accordingly. Moreover, it reflects the fact that it is less harmful to confuse some classes than others because the responses may be similar or the same. Thus, based on above scoring metric, a set of cardiac abnormalities are identified as a set scoring classes. In context of the above scoring metric and the set of scoring classes defined, those recordings, from among the ECG recordings, that belong to at least one disease/cardiac abnormality from among the scoring classes are filtered and considered for training. Thus, at step 306 of the method 300, the one or more hardware processors 104 prune the down sampled plurality of ECG recordings to generate a pruned training dataset by eliminating one or more ECG recordings that fail to capture cardiac abnormality among the set of cardiac abnormalities identified by the set scoring classes. In one implementation, since the performance of the classification models would be quantified based on 27 (scoring classes) of the 117 classes, for a more focused approach, the training dataset is pruned by eliminating all recordings that are not labeled at least by one of the recordings which contains at least one class from the scoring group.

At step 308 of the method 300, the one or more hardware processors 104 slice each ECG recording in the pruned training data set to generate a windowed dataset of overlapping windows. Each recording is segmented into a 5 s window with 50% overlap. The slicing enables reducing discrepancy between length of different ECG recordings, while the 50% overlap enables keeping all parts of the window into focus.

Data Slicing (windowing): Let $L_s$ represent an instance of 12-lead ECG recording with sampling frequency of $f_s$ Hz. For the present application, each instance of ECG recording is segmented into 5 second-wide windows with 50% overlap. Since the dataset has non-uniform recording time-lengths as depicted in FIG. 4B, a strategy enumerated in the following steps has been adapted for generating the 5 second windows: (i) For recordings with time length <5 secs: Zero-padding is used to make the recording lengths equal to 5 seconds and a single window is formed. (ii) For recordings with time length ≥5 secs but ≤30 secs: For recording meeting this criteria, W number of windows are extracted from the signal where W is defined as:

$$W_s = \frac{L_s - O_{ratio}}{L_w - O_{ratio}} \qquad (1)$$

Where, $L_s$ is the length of the recording, $L_w$ is the length of windows, $O_{ratio}$ is the overlapping ratio between contiguous pair of windows. The values of the parameters set for the present computation are: $L_w$=5 secs, $O_{ratio}$=0.5. For a 30 second recording, the maximum value that W can attain is 11. (iii) For recordings with time length >30 secs: Windows are generated from the middle of the recording based on equation (1) with $L_w$=5 secs, $O_{ratio}$=0.

At step 310 of the method 300, the one or more hardware processors 104 apply the fulcrum-based data rebalancing technique on the windowed dataset to generate the rebalanced training dataset for the multiclass-multilabel cardiac abnormalities. The fulcrum-based data rebalancing technique comprising:

a) Deriving a fulcrum point ($N_{fulcrum}$) of the windowed dataset from class frequency of each window in the windowed dataset based on one or more class labels from among the set of scoring classes assigned to each window. The more classes from among the set of scoring classes with class frequency above the fulcrum point are identified as majority classes, wherein classes with class frequency below the fulcrum point are identified as minority classes.

b) Further, performing random sampling on the windowed dataset that is identified under minority classes to reach the fulcrum point, wherein random sampling provides a representation at least equal to the fulcrum point to the minority classes.

Existing data balancing algorithms are designed for binary/multi-class datasets. These algorithms balance the datasets in terms of the most-represented class. High disparity exists among natural datasets (especially clinical data). This results in ballooning of the rebalanced dataset, also the natural balance of the dataset is completely overhauled, following such practices. For the multi class-multi label data imbalance problem, the fulcrum based data rebalancing disclosed herein is based on three objectives: maintain natural balance of the data, control the re-sample volume, and still support the lowly represented classes there by aiding proper training of the deep learning (DL) based HNN architecture. Thus, fulcrum based data re-balancing reduces the bias introduced in the model, contributing to improving model accuracy of the HNN architecture in turn improving the multi-class classification or prediction of cardiac abnormality. As has been mentioned earlier, the total 43101 recordings that constitute the training dataset are labelled with 117 classes with multi-label instances being the majority. Among the 17 classes, only 27 classes have been identified to be relevant for scoring. Hence for training the HNN architecture, recordings that has at least one scoring labels tagged to it have been considered. It is found that among the 43101 training recordings only 33000 recordings meet that criteria. A histogram of the 27 scoring labels among the 22K recordings are plotted in FIG. 4C. It can be observed from the plot that there exists an extremely high imbalance even among the scoring classes as well. While a single class (Normal Sinus rhythm) cover almost 40% of the training instances, the rest of the 26 classes cover the rest. Also, it can be observed that the 10 least represented classes constitute approximately only 5% of the total training population. Performance of the HNN based classification models are highly dependent upon the volume of training data. Thus, at first the fulcrum point $N_{fulcrum}$ is obtained based on which the training dataset is rebalanced. The strategy involves random resampling of the minority classes. Now in order to boost the representation of the minority classes, the following steps are executed and represented with pseudocode in Algorithm 1.

a) Read multiclass training labels.
b) Find distribution of the scoring classes form the labels
c) Find the fulcrum point(total class representations/scoring class count)
d) For classes with representations less than the fulcrum point, random resampling is done from the representations till fulcrum point is reached.
e) No processing is done for classes with representations more than the fulcrum point

---

Algorithm 1: Fulcrum Based Re-balancing Algorithm ($X_{N \times L \times M}$, $A_{N \times C}$, C):

---

$X_{N \times L \times M}$= training data, $A_{N \times C}$ = annotation, N = recording count, L = lead count, M = sample points in each recording window, C = class count 1:   function FULCRUM(X, A, C)

2:    $D_{1 \times C} \leftarrow \sum_{n=1}^{N} A$         /Computing class distribution/

3:    $N_{fulcrum} = \frac{1}{C} \sum_{i=1}^{C} D_i$      /Finding the fulcrum point/

4:   for k ← 1 to C do
5:    while $D_k < N_{fulcrum}$ do         / Data proning applied to minority classes/
6:     $X^k$, $A^k \leftarrow \{x \subset X, a \subset Ala_{all,k} = 1\}$ /Subset bearing kth class/
7:     $X^R$, $A^R \leftarrow$ random_sample $X^k$, $A^k$/One random sample of kth class/
8:     $X \leftarrow X \cup X^R$
9:     $A \leftarrow A \cup A^R$
10:    $D_k \leftarrow D_k + 1$
11:    end while
12:    end for
13:    end function

---

It is ensured that following this process, all the minority class representations are at least equal to $N_{fulcrum}$. The above strategy is based on re-sampling of the minority classes and no data proning is applied to the majority classes in order to waste any data. The effect of the classification model performance due to the data augmentation and balancing has been found to be positive. The quantitative results are reported and analyzed in results section.

Thus, advantage of the fulcrum based data re-balancing strategy over existing data re-balancing strategies is that it identifies the most represented classes, treats that rest of the classes as minority and augments them to match the majority class. The success of any data balancing is very much dependent upon the majority class count. In worst case, the count of the re-balanced data set can balloon and be unmanageable for standard computing systems. However, the fulcrum based data re-balancing strategy disclosed herein keeps the volume of dataset after rebalancing under control in a relative sense.

Figure 1B:
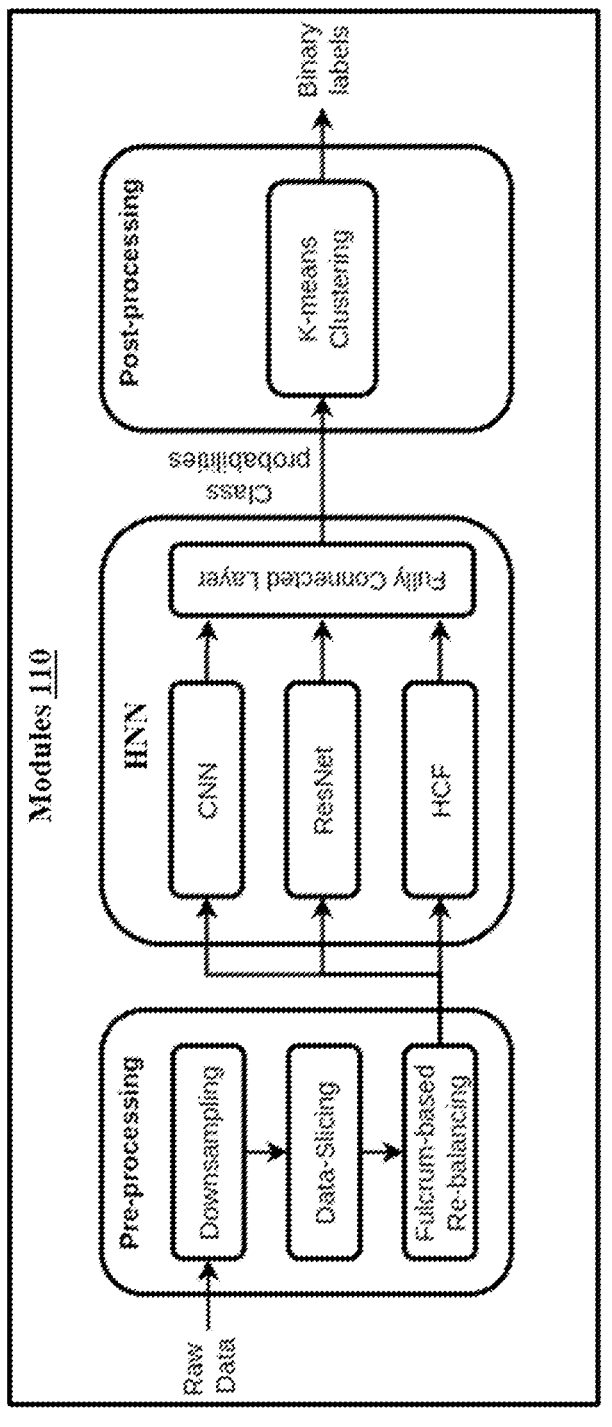
FIG. 1B is an overview of the system architecture depicting ECG classification pipeline for identifying cardiac abnormalities, in accordance with some embodiments of the present disclosure.
Figure 2A:
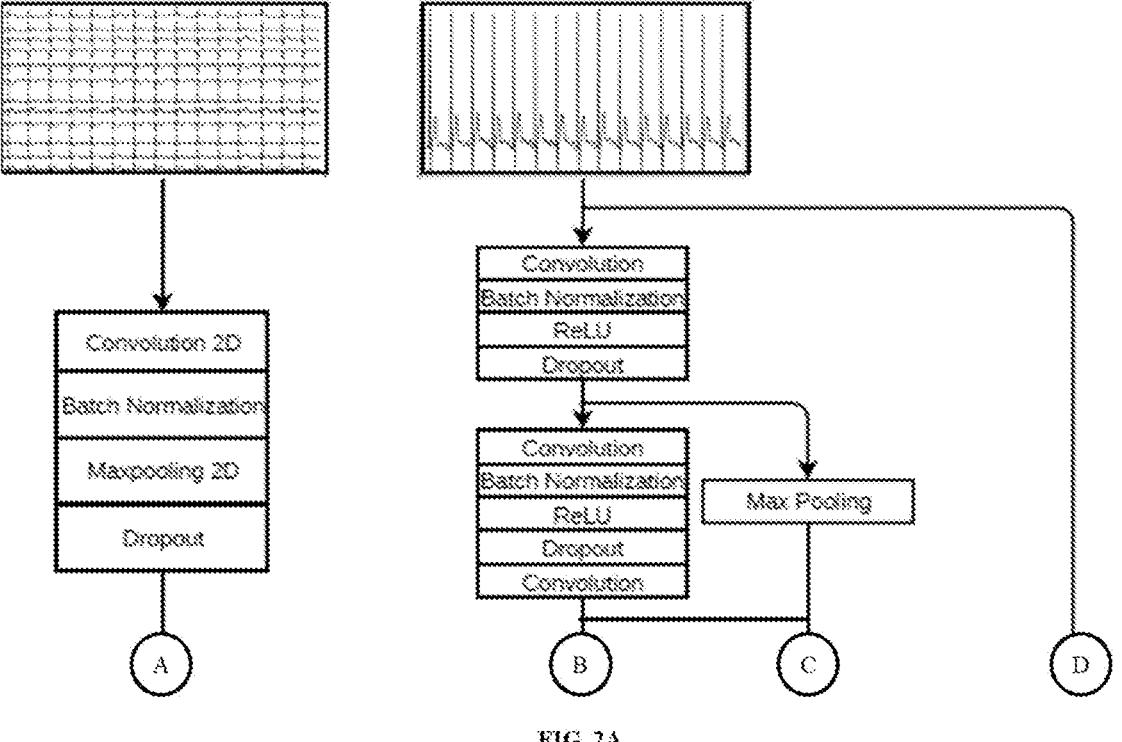
FIGS. 2A, 2B, AND 2C (collectively referred as FIG. 2) illustrates an architectural overview of the HNN used by the system of FIG. 1, in accordance with some embodiments of the present disclosure.
Figure 2B:
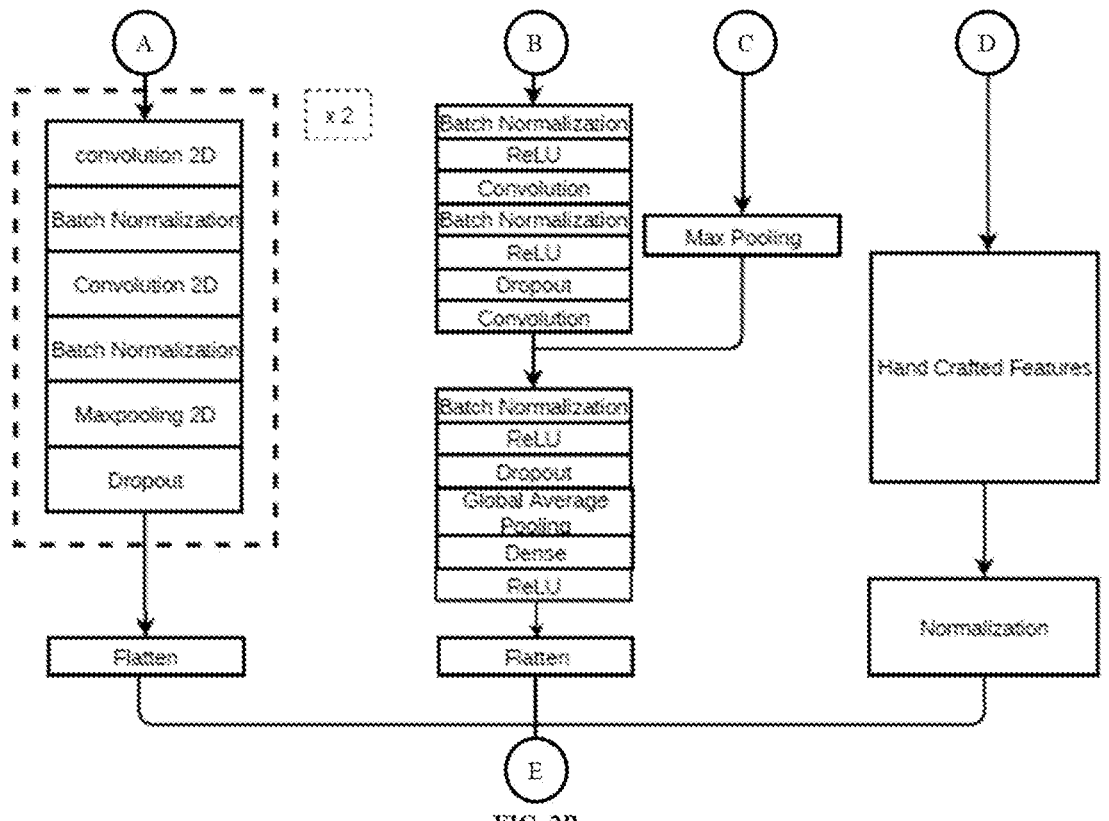
Figure 2C:
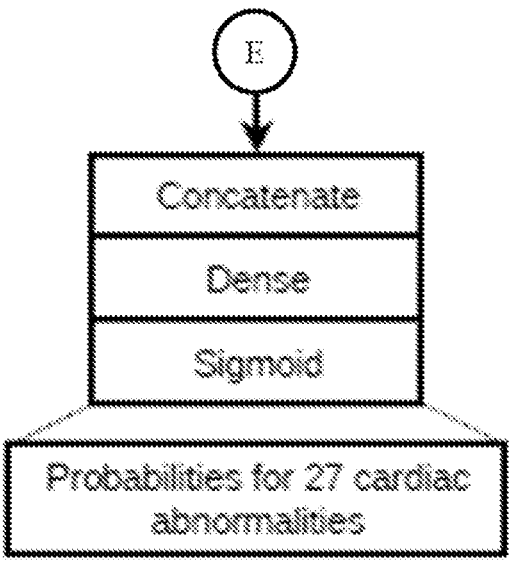

Steps 304, 306, 308 and 310 correspond to the preprocessing block as depicted in FIG. 1B. The pre-processing approach applied on the ECG recordings improves the quality of training data to be used, effectively contributing to improving model prediction accuracy.

Once the ECG data recordings are preprocessed, then at step 312 of the method 300, the one or more hardware processors 104 train the DL model based on the Hybrid Neural Network (HNN) based on the rebalanced training dataset to classify input ECG signals. The rebalanced data set is split into training and validation dataset for DL model training. As depicted in FIG. 2 The HNN has 3 parallel layers comprising: (i) a Convolutional Neural Network (CNN) layer receiving a multi-lead ECG input of the subject to learn a set of abstracted features, (ii) a Residual Network (ResNet) layer receiving a single lead ECG input to learn discriminating features associated with the heart activity of the subject, and (iii) a layer comprising a set of handcrafted features derived from raw data of the single lead ECG input. The CNN layer that generates abstracted features by deep learning network after each layer (output of convolution between input data and selected kernel), the ResNet layer that generates low-level general features in its beginning and complex (discriminating) features associated with the application domain in the later stages, and the set of handcrafted features which are statistical and morphological engineered features are concatenated in final stage to predict the cardiac abnormalities identified in the input ECG into one or more classes among the set of scoring classes.

As depicted in FIG. 2, the CNN layer is a 5 layered structure, which takes 12 leads of raw ECG data as input. The architecture has 3 blocks out of which 2 are identical. First layer of the first block is 2D convolutional layer followed by a batch normalization and 2D max-pooling with a decimation factor of 3. Second and third blocks are identical and consists of two 2D convolutional layers. Each convolution layer is followed by a batch-normalization, and each second batch-normalization is followed by a 2D max-pooling layer with decimation factor of 2. To prevent overfitting during training, a dropout layer is used in the end of each block with 20% dropout change in first and second block and 50% dropout change in third block. 32 filters are used in all convolutional layers with kernel size of 3 in 8.

The ResNet layer of the HNN is a reduced 34 layered ResNet, which is based on the state-of-the-art technique '*Cardiologist-level arrhythmia detection and classification in ambulatory electrocardiograms using a deep neural network*' by Hannun et. al., which takes only one lead of raw ECG data. The Resnet layer consists of 2 residual blocks with two convolutional layers per block. The convolutional layers have a filter width of 16 and 64 filters. Every alternate residual block subsamples its inputs by a factor of 2. Before each convolutional layer, batch normalization and a rectified linear activation is applied. Further, a Dropout layer is applied between the convolutional layers and after the nonlinearity with a probability of 0.25.

The third layer is of the Hand Crafted Features (HCF), which are integrated in the last concatenation layer of the HNN. The complete list of features are provided in TABLE 1.

TABLE 1

| Index | Features |
|---|---|
| 1. | Mean |
| 2. | Median |
| 3. | Standard Deviation |
| 4. | Skewness |
| 5. | Kurtosis |
| 6. | Age |
| 7. | Sex |

Hand Crafted Features (HCF) description: The features are defined on the respective time series/frequency domain data considering a set of sample points {xi}, where i={1,2, 3, . . . , n} are total N instances covering the whole set of available data length.

1) The mean is the simple arithmetic mean of the data points, defined by mean, $$\bar{x} = (\Sigma x)/N \tag{2}$$

2) Median is the middle most value of the data series. The middle number in a sorted list of numbers can be more descriptive of that data set than the average.

3) Standard deviation measures the dispersion of a dataset relative to its mean and is given by, $$\sigma = \sqrt{\Sigma(x^i - \bar{x})^2/N} \tag{3}$$

4) The skewness of the set defines the asymmetry of the distribution and the Pearsonian measure of skewness is calculated by the formula, $$\text{Skewness } (\mu_3) = (\Sigma(x_i - \bar{x})^3)/N \tag{4}$$

5) The Kurtosis of the set that defines how heavily the tails of a distribution differ from the tails of a normal distribution. Kurtosis identifies whether the tails of a given distribution contain extreme values and is defined by the formula, $$\text{Kurtosis} = (\mu_4) = (\Sigma(x_i - \bar{x})^4)/N \tag{5}$$

Once the preprocessed data is processed by the HNN then as depicted in FIG. 1B post processing is performed on the HNN output, wherein the confidence score arrays of 5 s windows from an ECG recording are averaged together to obtain one confidence array per recording. Afterward, k-means is applied to the averaged confidence array of 27 elements to form two clusters and one of which is considered to be the identified set of classes in the ECG recording.

Figures 4C, 5A:
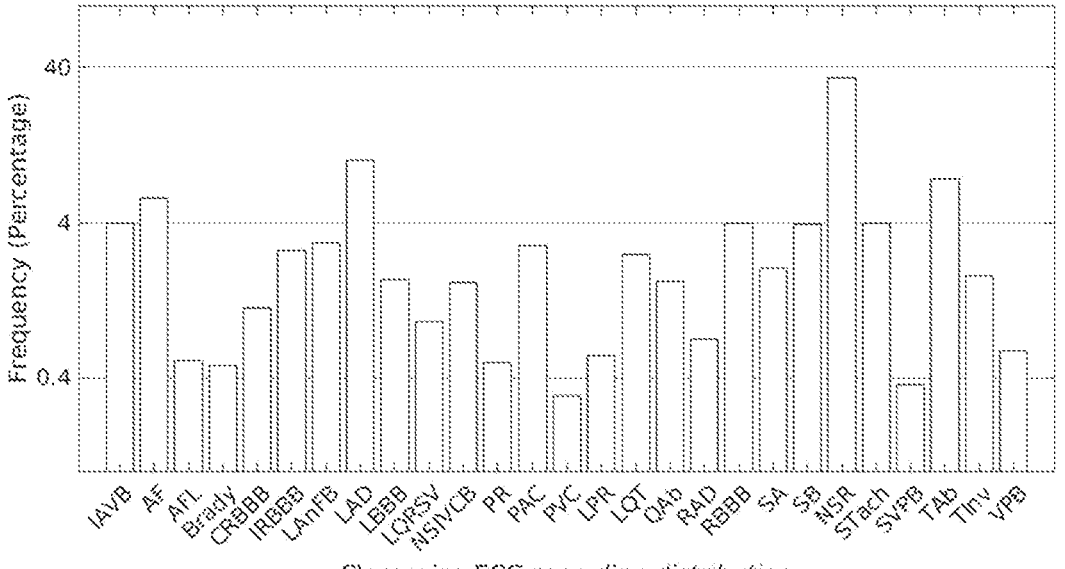
FIGS. 5A, 5B, AND 5C are graphical illustrations depicting performance of the system 100, in accordance with some embodiments of the present disclosure.
Figure 5B:
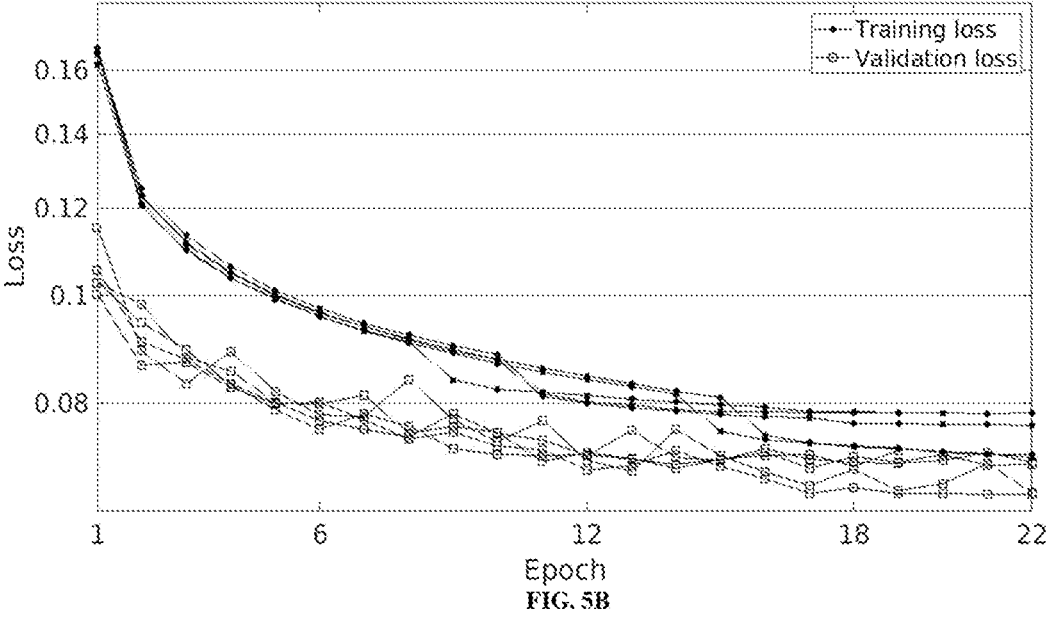
Figure 5C:
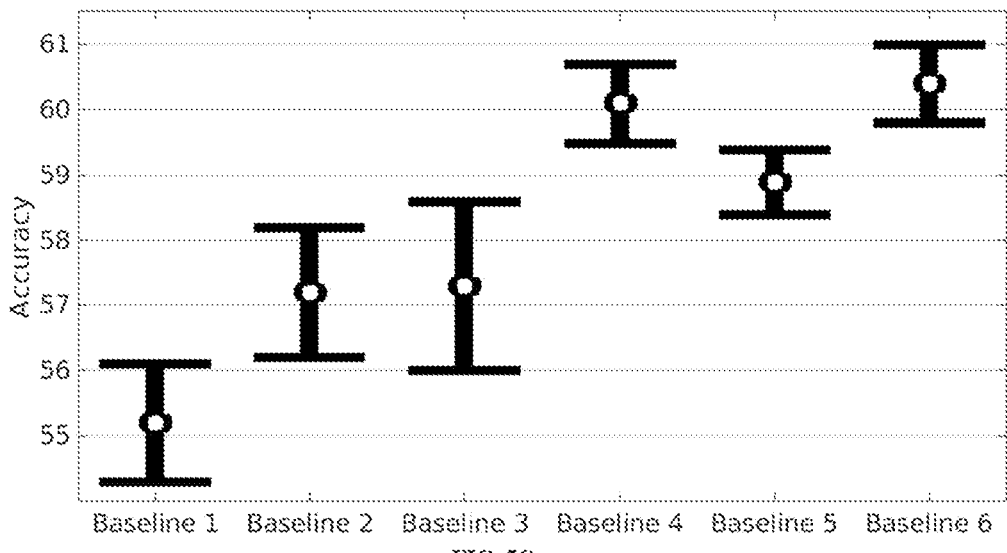

RESULTS AND COMPARISONS: FIGS. 5A through 5C are graphical illustrations depicting performance of the system 100, in accordance with some embodiments of the present disclosure. All evaluations were trained on the publicly available training dataset. The trained DL models were tested on a subsection of the hidden dataset. All approaches pertaining to the baselines 2 is a modified version of the preceding one. The DL model is trained on 80% of the training data and tested the performance of the trained model on the rest 20%. The challenge metric score obtained was relied upon and looked for improvement in the score.

Validation methodology: Python 3.6.9, Tensorflow 2.2.0, and a runner One Nvidia Tesla V100 GPU with 32 GB VRAM (video Random Access Memory) are used in all experiments. The potential efficacy of the different baselines discussed is compared using stratified 5-fold cross validation. The cross-validation folds are set up so that no segments from the same recording appear in both the train and test data, and 10% of the training data is taken for the validation. The performance metrics used for the model evaluation are described in the following paragraph.

Let A be the binary-class confusion matrix (cm) with element $A_{c,i,j}$ for each class c where, i represents the predicted class, and j represents the actual class and true positive, false positive, false negative and true negative are defined as $tp = A_{c,1,1}$, $fp = A_{c,1,0}$, $fn = A_{c,0,1}$ and $tn = A_{c,0,0}$. Sensitivity (true positive rate), Specificity (true negative rate) and precision (positive predictive value) are presented in equation below.

$$tpr = \frac{tp}{tp + fn}; tnr = \frac{tnp}{fp + tn}; ppv = \frac{tp}{tp + fp} \tag{6}$$

1. AUROC: The area under the receiver operating characteristic (ROC) is used to determine the trade-off between (tpr) and (tpr) across multiple decision thresholds t.

$$AUROC_c = 0.5 \times (tpr_{t+1} - tpr_t) \times tnr_{t+1} + tnr_t) \tag{7}$$

2. AUPRC: The area under the precision-recall curve is used to determine the trade-off between precision and recall across different decision thresholds.

$$AUPRC_c = (tpr_{t+1} - tpr_t) \times ppv_{t+1}) \tag{8}$$

3. F measure: It is the harmonic mean of precision and recall which measures the incorrectly classified cases in imbalanced data.

$$F = \frac{2 \times tp}{2 \times tp + fp + fn} \tag{9}$$

4. $F_\beta$ measure: It is the weighted harmonic mean of precision and recall, where the $\beta$ parameter determines the weight of recall in combined score. The value of $\beta$ used here is 2.

5.

$$F_\beta = \frac{(1 + \beta^2) \times tp}{(1 + \beta^2) \times tp + fp + \beta^2 \times fn} \tag{10}$$

$$G_\beta \text{ measure, } G_\beta = \frac{tp}{tp + fp + \beta \times fn} \tag{11}$$

6. Challenge metric: The Challenge metric or Normalized score ($N_s$) gives the classifier full credit for correct diagnoses (true positives), partial credit for clinical errors with equal risks or outcomes (false negatives), and a penalty for false positives. It is defined as the observed score $O_s$ normalized between correct score $C_s$ and inactive score $t_s$ in equation below:

$$O_s = \Sigma(weights \times A_O), C_s = \Sigma(weights \times A_C), I_s = \Sigma(weights \times A_I) \tag{12}$$

where, weights are the weight matrix provided in [ref], and $A_O$ is the cm for the observed classifier, $A_c$ is cm for the true classifier which always gives the correct labels and $A_I$ is the cm for the incorrect classifier which always chooses the normal class.

$$N_s = \frac{O_s - I_s}{C_s - I_s} \tag{13}$$

RESULTS: For the validation purpose, the classification performances of the baselines have been quantified based upon multiple metrics mentioned above. All such scores in (mean±standard deviation) format generated from the 5-fold cross validation scores, are presented in TABLE 2.

TABLE 2

| Baseline | AUROC | AUPRC | F measure | $F_\beta$ measure | $G_\beta$ measure | Challenge metric |
|---|---|---|---|---|---|---|
| 1 | 92.2 ± 0.2 | 50.6 ± 1.3 | 46.1 ± 0.8 | 48.4 ± 0.5 | 28.0 ± 0.6 | 55.2 ± 0.9 |
| 2 | 92.8 ± 0.5 | 52.6 ± 1.6 | 48.0 ± 1.7 | 50.1 ± 1.6 | 29.4 ± 1.0 | 57.2 ± 1.0 |
| 3 | 92.8 ± 0.5 | 52.0 ± 1.5 | 48.2 ± 1.5 | 50.2 ± 1.3 | 29.5 ± 1.0 | 57.3 ± 1.3 |
| 4 | 94.4 ± 0.3 | 55.8 ± 0.7 | 51.9 ± 0.8 | 54.3 ± 0.9 | 32.4 ± 0.5 | 60.1 ± 0.6 |
| 5 | 93.7 ± 0.2 | 55.4 ± 0.9 | 52.2 ± 0.7 | 56.2 ± 0.7 | 31.9 ± 0.5 | 58.9 ± 0.5 |
| 6 | 94.1 ± 0.2 | 56.2 ± 0.7 | 53.0 ± 0.4 | 56.8 ± 0.4 | 32.5 ± 0.4 | 60.4 ± 0.6 |

It can be observed from the TABLE 2 that multiple metric scores increase monotonically from Baseline 1 to Baseline 6 with an exception for Baseline 5. Hence it can be summarized that each addition of algorithm component to the Baselines has further strengthened the classification performance. It can be further observed from the TABLE 2 that Baseline 6 has generated the highest scores except AUROC as compared to all the other baseline performances. This indicates that Baseline 6 is the most suitable version of the algorithm for the Multi-lead EGG classification task. A confirmation regarding the correct choice of the final version of the classification algorithm is visible in FIG. 5C. The figure plots the 5-fold cross-validation Challenge metric scores for all the baselines. In the figure, the heights of the bar represents the standard deviation, and the red-markers indicate the mean value scores for the baselines. It can be observed from the figure that Baseline 6 gives the best mean-standard deviation combination among all the baselines.

The training-loss and validation-loss scores obtained during the 5-fold cross validation evaluation of Baseline 6 are plotted in FIG. 5B. From the figure it can be observed that there exists a positive bias between the training and validation curves for all the 5-folds. Such a bias indicates the genetic and robust design of the classification algorithm. A similar pattern can be observed in FIG. 5A, where the corresponding accuracy scores have been plotted. The Baseline 6 performance has been further compared with existing state-of-the-art ECG classification algorithm. The comparison is presented in TABLE 3.

TABLE 3

| Approach line | AUROC | AUPRC | F measure | $F_\beta$ measure | $G_\beta$ measure | Challenge metric |
|---|---|---|---|---|---|---|
| Stanford | 90.2 ± 0.2 | 43.9 ± 0.5 | 43.0 ± 1.1 | 45.4 ± 1.1 | 26.4 ± 0.9 | 49.9 ± 0.7 |
| Method 300 | 94.1 ± 0.2 | 56.2 ± 0.7 | 53.0 ± 0.4 | 56.8 ± 0.4 | 32.5 ± 0.4 | 60.4 ± 0.6 |

A State of the Art (SoA) ECG classification algorithm selected for the comparison is developed by Stanford group. From the tabulated values, it can be clearly observed that the disclosed ECG classification algorithm has produced better classification performance as compared to the SoA.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for identifying cardiac abnormalities in multi-lead electrocardiograms (ECGs), the method comprising:

receiving, via one or more hardware processors, a training data set comprising a plurality of ECG recordings with multilabel-multiclass cardiac abnormalities, wherein each of the plurality of ECGs are sampled at varying frequencies;

down sampling, via the one or more hardware processors, the plurality of ECG recordings with a single frequency pre-identified statistically;

pruning, via the one or more hardware processors, the down sampled plurality of ECG recordings to generate a pruned training dataset by eliminating one or more ECG recordings that fail to capture information related to at least one cardiac abnormality among a set of cardiac abnormalities identified as a set scoring classes;

slicing, via the one or more hardware processors, each ECG recording in the pruned training data set to generate a windowed dataset of overlapping windows, and each ECG recording is segmented into predefined seconds window with a predefined percentage overlap, wherein the slicing reduces discrepancy between length of varied ECG recordings and the predefined percentage overlap enables to maintain all parts of the predefined seconds window into focus;

applying, via the one or more hardware processors, a fulcrum-based data rebalancing technique on the windowed dataset to generate a rebalanced training dataset for the multiclass-multilabel cardiac abnormalities, and the fulcrum-based data rebalancing enables modifying existing balance in data being skewed in nature to maintain natural balance of the data and controls re-sample volume while supporting the lowly represented classes, wherein the fulcrum-based data rebalancing technique reduces bias introduced in a Deep Learning model (DL) model contributing to accuracy of a Hybrid Neural Network (HNN) architecture thereby improving multiclass classification or prediction of cardiac abnormality, wherein the fulcrum-based data rebalancing technique identifies most represented classes, treats rest of the classes as minority, augments rest of the classes to match the majority class, and the fulcrum-based data re-balancing technique maintains volume of dataset after rebalancing under control, wherein the fulcrum-based data rebalancing technique comprising:

deriving a fulcrum point ($N_{fulcrum}$) of the windowed dataset from class frequency of each window in the windowed dataset based on one or more class labels from among the set of scoring classes assigned to each window, wherein one or more classes from among the set of scoring classes with class frequency above the fulcrum point are identified as majority classes, wherein classes with class frequency below the fulcrum point are identified as minority classes; and performing a random sampling on the windowed dataset that is identified under minority classes to reach the fulcrum point, wherein random sampling provides a representation at least equal to the fulcrum point to the minority classes, wherein the majority classes are excluded from the random sampling; and training, via the one or more hardware processors, the HNN architecture based DL model using the rebalanced training dataset to classify input ECG signals.

2. The processor implemented method of claim 1, further comprising utilizing the trained DL model to classify an input ECG signal of a subject by predicting the cardiac abnormalities in the input ECG into one or more classes among the set of scoring classes.

3. The processor implemented method of claim 2, wherein the HNN has three parallel layers comprising:

(i) a Convolutional Neural Network (CNN) layer receiving a multi-lead ECG input of the subject to learn a set of abstracted features, (ii) a Residual Network (ResNet) layer receiving a single lead ECG input to learn discriminating features associated with the heart activity of the subject, and (iii) a layer comprising a set of handcrafted features derived from raw data of the single lead ECG input, and wherein the CNN layer, the ResNet layer and the set of handcrafted features are concatenated to predict the cardiac abnormalities in the input ECG into one or more classes among the set of scoring classes, wherein the set of handcrafted features derived from the input ECG are concatenated prior to predicting multiclass output for the ECG signal and number of features are flexible, enables adding domain-specific features as needed.

4. The processor implemented method of claim 1, wherein the fulcrum-based data rebalancing technique maintains natural balance of the windowed dataset, controls re-sample volume, and supports lowly represented classes for training of the HNN.

5. A system for identifying cardiac abnormalities in multi-lead electrocardiograms (ECGs), the system comprising:

a memory storing instructions;

one or more Input/Output (I/O) interfaces; and one or more hardware processors coupled to the memory via the one or more I/O interfaces, wherein the one or more hardware processors are configured by the instructions to:

receive a training data set comprising a plurality of ECG recordings with multilabel-multiclass cardiac abnormalities, wherein each of the plurality of ECGs are sampled at varying frequencies;

down sample the plurality of ECG recordings with a single frequency pre-identified statistically;

prune the down sampled plurality of ECG recordings to generate a pruned training dataset by eliminating one or more ECG recordings that fail to capture information related to at least one cardiac abnormality among a set of cardiac abnormalities identified as a set scoring classes;

slice each ECG recording in the pruned training data set to generate a windowed dataset of overlapping windows, and each ECG recording is segmented into predefined seconds window with a predefined percentage overlap, wherein the slicing reduces discrepancy between length of varied ECG recordings and the predefined percentage overlap enables to maintain all parts of the predefined seconds window into focus;

apply a fulcrum-based data rebalancing technique on the windowed dataset to generate a rebalanced training dataset for the multiclass-multilabel cardiac abnormalities, and the fulcrum-based data rebalancing enables modifying existing balance in data being skewed in nature to maintain natural balance of the data and controls re-sample volume while supporting the lowly represented classes, wherein the fulcrum-based data rebalancing technique reduces bias introduced in a Deep Learning model (DL) model contributing to accuracy of a Hybrid Neural Network (HNN) architecture thereby improving multi-class classification or prediction of cardiac abnormality, wherein the fulcrum-based data rebalancing technique identifies most represented classes, treats rest of the classes as minority, augments rest of the classes to match the majority class, and the fulcrum-based data re-balancing technique maintains volume of dataset after rebalancing under control, wherein the fulcrum-based data rebalancing technique comprising:

deriving a fulcrum point ($N_{fulcrum}$) of the windowed dataset from class frequency of each window in the windowed dataset based on one or more class labels from among the set of scoring classes assigned to each window, wherein one or more classes from among the set of scoring classes with class frequency above the fulcrum point are identified as majority classes, wherein classes with class frequency below the fulcrum point are identified as minority classes; and performing a random sampling on the windowed dataset that is identified under minority classes to reach the fulcrum point, wherein random sampling provides a representation at least equal to the fulcrum point to the minority classes, wherein the majority classes are excluded from the random sampling; and train the HNN architecture based DL model using the rebalanced training dataset to classify input ECG signal.

6. The system of claim 5, wherein the one or more hardware processors are configured to utilize the trained DL model to classify an input ECG signal of a subject by predicting the cardiac abnormalities in the input ECG into one or more classes among the set of scoring classes.

7. The system of claim 6, wherein the HNN has three parallel layers comprising:

(i) a Convolutional Neural Network (CNN) layer receiving a multi-lead ECG input of the subject to learn a set of abstracted features, (ii) a Residual Network (ResNet) layer receiving a single lead ECG input to learn discriminating features associated with the heart activity of the subject, and (iii) a layer comprising a set of handcrafted features derived from raw data of the single lead ECG input, and wherein the CNN layer, the ResNet layer and the set of handcrafted features are concatenated to predicting the cardiac abnormalities in the input ECG into one or more classes among the set of scoring classes, wherein the set of handcrafted features derived from the input ECG are concatenated prior to predicting multiclass output for the ECG signal and number of features are flexible, enables adding domain-specific features as needed.

8. The system of claim 5, wherein the one or more hardware processors are further configured to maintain natural balance of the windowed dataset, control re-sample volume, and support lowly represented classes for training of the HNN via the fulcrum-based data rebalancing technique.

9. One or more non-transitory machine-readable information storage mediums comprising one or more instructions which when executed by one or more hardware processors cause:

receiving, a training data set comprising a plurality of ECG recordings with multilabel-multiclass cardiac abnormalities, wherein each of the plurality of ECGs are sampled at varying frequencies;

down sampling, via the one or more hardware processors, the plurality of ECG recordings with a single frequency pre-identified statistically;

pruning, via the one or more hardware processors, the down sampled plurality of ECG recordings to generate a pruned training dataset by eliminating one or more ECG recordings that fail to capture information related to at least one cardiac abnormality among a set of cardiac abnormalities identified as a set scoring classes;

slicing, via the one or more hardware processors, each ECG recording in the pruned training data set to generate a windowed dataset of overlapping windows, and each ECG recording is segmented into predefined seconds window with a predefined percentage overlap, wherein the slicing reduces discrepancy between length of varied ECG recordings and the predefined percentage overlap enables to maintain all parts of the predefined seconds window into focus;

applying, via the one or more hardware processors, a fulcrum-based data rebalancing technique on the windowed dataset to generate a rebalanced training dataset for the multiclass-multilabel cardiac abnormalities, and the fulcrum-based data rebalancing enables modifying existing balance in data being skewed in nature to maintain natural balance of the data and controls re-sample volume while supporting the lowly represented classes, wherein the fulcrum-based data rebalancing technique reduces bias introduced in a Deep Learning model (DL) model contributing to accuracy of a Hybrid Neural Network (HNN) architecture thereby improving multi-class classification or prediction of cardiac abnormality, wherein the fulcrum-based data rebalancing technique identifies most represented classes, treats rest of the classes as minority, augments rest of the classes to match the majority class, and the fulcrum-based data re-balancing technique maintains volume of dataset after rebalancing under control, wherein the fulcrum-based data rebalancing technique comprising:

deriving a fulcrum point ($N_{fulcrum}$) of the windowed dataset from class frequency of each window in the windowed dataset based on one or more class labels from among the set of scoring classes assigned to each window, wherein one or more classes from among the set of scoring classes with class frequency above the fulcrum point are identified as majority classes, wherein classes with class frequency below the fulcrum point are identified as minority classes; and performing a random sampling on the windowed dataset that is identified under minority classes to reach the fulcrum point, wherein random sampling provides a representation at least equal to the fulcrum point to the minority classes, wherein the majority classes are excluded from the random sampling; and training, via the one or more hardware processors, the HNN architecture based DL model using the rebalanced training dataset to classify input ECG signals.

10. The one or more non-transitory machine-readable information storage mediums of claim 9, wherein the one or more instructions which when executed by the one or more hardware processors further cause utilizing the trained DL model to classify an input ECG signal of a subject by predicting the cardiac abnormalities in the input ECG into one or more classes among the set of scoring classes.

11. The one or more non-transitory machine-readable information storage mediums of claim 10, wherein the one or more instructions which when executed by the one or more hardware processors further cause:

(i) a Convolutional Neural Network (CNN) layer receiving a multi-lead ECG input of the subject to learn a set of abstracted features, (ii) a Residual Network (ResNet) layer receiving a single lead ECG input to learn discriminating features associated with the heart activity of the subject, and (iii) a layer comprising a set of handcrafted features derived from raw data of the single lead ECG input, and wherein the CNN layer, the ResNet layer and the set of handcrafted features are concatenated to predict the cardiac abnormalities in the input ECG into one or more classes among the set of scoring classes, wherein the set of handcrafted features derived from the input ECG are concatenated prior to predicting multiclass output for the ECG signal and number of features are flexible, enables adding domain-specific features as needed.

12. The one or more non-transitory machine-readable information storage mediums of claim 9, wherein the fulcrum-based data rebalancing technique maintains natural balance of the windowed dataset, controls re-sample volume, and supports lowly represented classes for training of the HNN.

* * * * *